United States Patent
Lee et al.

(10) Patent No.: US 10,961,554 B2
(45) Date of Patent: Mar. 30, 2021

(54) PROMOTER AND A METHOD FOR PRODUCING L-AMINO ACID USING THE SAME

(71) Applicant: CJ CHEILJEDANG CORPORATION, Seoul (KR)

(72) Inventors: Ji Yeon Lee, Seoul (KR); Jin Sook Chang, Seoul (KR); Hyung Joon Kim, Seoul (KR); Byoung Hoon Yoon, Seoul (KR); Sun Hyoung Choi, Seoul (KR); Yunjung Choi, Seoul (KR)

(73) Assignee: CJ Cheiljedang Corporation, Seoul (KR)

( * ) Notice: Subject to any disclaimer, the term of this patent is extended or adjusted under 35 U.S.C. 154(b) by 0 days.

(21) Appl. No.: 16/639,364

(22) PCT Filed: Mar. 27, 2019

(86) PCT No.: PCT/KR2019/003565
§ 371 (c)(1),
(2) Date: Feb. 14, 2020

(87) PCT Pub. No.: WO2019/190192
PCT Pub. Date: Oct. 3, 2019

(65) Prior Publication Data
US 2020/0248217 A1    Aug. 6, 2020

(30) Foreign Application Priority Data
Mar. 27, 2018    (KR) .................. 10-2018-0035156

(51) Int. Cl.
| | | |
|---|---|---|
| *C12P 13/04* | (2006.01) | |
| *C12N 9/10* | (2006.01) | |
| *C12N 9/14* | (2006.01) | |
| *C12N 15/77* | (2006.01) | |
| *C12N 1/21* | (2006.01) | |
| *C12P 13/14* | (2006.01) | |

(52) U.S. Cl.
CPC ............ *C12P 13/04* (2013.01); *C12N 9/1077* (2013.01); *C12N 9/14* (2013.01); *C12N 15/77* (2013.01); *C12P 13/14* (2013.01); *C12Y 204/02017* (2013.01); *C12Y 306/01031* (2013.01); *C12N 2830/55* (2013.01)

(58) Field of Classification Search
None
See application file for complete search history.

(56) References Cited

U.S. PATENT DOCUMENTS

2003/0113883 A1* 6/2003 Liaw .................. C12R 1/15
435/106
2016/0326556 A1* 11/2016 Wen ............... C12Y 503/01009

FOREIGN PATENT DOCUMENTS

| KR | 10-2013-0130377 | 12/2013 |
| KR | 10-2015-0143699 | 12/2015 |
| KR | 10-2016-0072278 | 6/2016 |

OTHER PUBLICATIONS

Kwon et al., Cloning of the histidine biosynthetic genes from Corynebacterium glutamicum, Can. J. Microbiol. 46, 2000, 848-55. (Year: 2000).*
Zhang et al., Ribosome binding site libraries and pathway modules for shikimic acid synthesis with Corynebacterium glutamicum, Microbial Cell Factories 14, 2015, 71. (Year: 2015).*
GenBank: CP025534.1, Corynebacterium glutamicum strain HA chromosome, complete genome, (665 pages) Dec. 27, 2017.
Kjeldsen, "Optimization of an industrial L-lysine producing Corynebacterium glutamicum strain," *DTU Library*, downloaded from orbit.dtu.dk on: Jun. 18, 2019 (188 pages).
Kulis-Horn et al., "Histidine biosynthesis, its regulation and biotechnological application in *Corynebacterium glutamicum*," *Microbial Biotechnology* 7(1):5-25 (2014).
Kulis-Horn et al., "*Corynebacterium glutamicum* ATP-phosphoribosyl transferases suitable for $_L$-histidine production—Strategies for the elimination of feedback inhibition," *Journal of Biotechnology* 206:26-37 (2015).
NCBI Reference Sequence: WP_003856149.1, "Multispecies: ATP phosphoribosyltransferase [Corynebacterium]," (1 page) (Aug. 29, 2013).
Schendzielorz et al., "Taking Control over Control: Use of Product Sensing in Single Cells to Remove Flux Control at Key Enzymes in Biosynthesis Pathways," *ACS Synth. Biol.* 3:21-29 (2014).
Schwentner et al., "Modular systems metabolic engineering enables balancing of relevant pathways for $_L$-histidine production with *Corynebacterium glutamicium*," *Biotechnol Biofuels* 12:65 (21 pages) (2019).

* cited by examiner

*Primary Examiner* — Robert B Mondesi
*Assistant Examiner* — Todd M Epstein
(74) *Attorney, Agent, or Firm* — Seed IP Law Group LLP

(57) ABSTRACT

The present disclosure relates to a novel promoter and a method for producing L-amino acids using the promoter, and more specifically, to a novel polynucleotide having promoter activity, a vector and a microorganism of the genus *Corynebacterium* comprising the polynucleotide, a method for producing L-amino acids and a fermented composition using the microorganism, and a fermented composition.

19 Claims, No Drawings

Specification includes a Sequence Listing.

SEQUENCE LISTING

<160> NUMBER OF SEQ ID NOS: 16

<210> SEQ ID NO 1
<211> LENGTH: 65
<212> TYPE: DNA
<213> ORGANISM: Corynebacterium glutamicum

<400> SEQUENCE: 1
aattattcga ctaatatcct cccccaaaca cacattgata actgttgtgt ggaagaatgt    60
accga                                                               65

<210> SEQ ID NO 2
<211> LENGTH: 65
<212> TYPE: DNA
<213> ORGANISM: Artificial Sequence
<220> FEATURE:
<223> OTHER INFORMATION: hisEG promoter

<400> SEQUENCE: 2
aattattcga ctaatatcct cccccaaaca cacattgata actgttgtgt ggtataatgt    60
accga                                                               65

<210> SEQ ID NO 3
<211> LENGTH: 65
<212> TYPE: DNA
<213> ORGANISM: Artificial Sequence
<220> FEATURE:
<223> OTHER INFORMATION: hisEG promoter

<400> SEQUENCE: 3
aattattcga ctaatatcct cccccaaaca cacattgata actgttgtgt ggtataatgg    60
accga                                                               65

<210> SEQ ID NO 4
<211> LENGTH: 75
<212> TYPE: DNA
<213> ORGANISM: Artificial Sequence
<220> FEATURE:
<223> OTHER INFORMATION: oligonucleotide

<400> SEQUENCE: 4
tcgtacagcg agtcaaatgt cttcactcgg tacattatac cacacaacag ttatcaatgt    60
gtgtttgggg gagga                                                    75

<210> SEQ ID NO 5
<211> LENGTH: 75
<212> TYPE: DNA
<213> ORGANISM: Artificial Sequence
<220> FEATURE:
<223> OTHER INFORMATION: oligonucleotide

<400> SEQUENCE: 5
tcgtacagcg agtcaaatgt cttcactcgg tccattatac cacacaacag ttatcaatgt    60
gtgtttgggg gagga                                                    75

<210> SEQ ID NO 6
<211> LENGTH: 33
<212> TYPE: DNA
<213> ORGANISM: Artificial Sequence
<220> FEATURE:
<223> OTHER INFORMATION: primer hisE-pro-2mt-AF

<400> SEQUENCE: 6

```
gatcctctag agtcgacttc gacgaatccc tcg                                    33
```

<210> SEQ ID NO 7
<211> LENGTH: 32
<212> TYPE: DNA
<213> ORGANISM: Artificial Sequence
<220> FEATURE:
<223> OTHER INFORMATION: primer hisE-pro-2mt-AR

<400> SEQUENCE: 7

```
cggtacatta taccacacaa cagttatcaa tg                                     32
```

<210> SEQ ID NO 8
<211> LENGTH: 32
<212> TYPE: DNA
<213> ORGANISM: Artificial Sequence
<220> FEATURE:
<223> OTHER INFORMATION: primer hisE-pro-2mt-BF

<400> SEQUENCE: 8

```
gtggtataat gtaccgagtg aagacatttg ac                                     32
```

<210> SEQ ID NO 9
<211> LENGTH: 32
<212> TYPE: DNA
<213> ORGANISM: Artificial Sequence
<220> FEATURE:
<223> OTHER INFORMATION: primer hisE-pro-2mt-BR

<400> SEQUENCE: 9

```
atgcctgcag gtcgactgat acccaaatcg ag                                     32
```

<210> SEQ ID NO 10
<211> LENGTH: 32
<212> TYPE: DNA
<213> ORGANISM: Artificial Sequence
<220> FEATURE:
<223> OTHER INFORMATION: primer hisE-pro-3mt-AR

<400> SEQUENCE: 10

```
cggtccatta taccacacaa cagttatcaa tg                                     32
```

<210> SEQ ID NO 11
<211> LENGTH: 32
<212> TYPE: DNA
<213> ORGANISM: Artificial Sequence
<220> FEATURE:
<223> OTHER INFORMATION: primer hisE-pro-3mt-BF

<400> SEQUENCE: 11

```
gtggtataat ggaccgagtg aagacatttg ac                                     32
```

<210> SEQ ID NO 12
<211> LENGTH: 34
<212> TYPE: DNA
<213> ORGANISM: Artificial Sequence
<220> FEATURE:
<223> OTHER INFORMATION: primer hisG(G233H/T235Q)-AF

<400> SEQUENCE: 12

```
gatcctctag agtcgacccc aaacaagggc tcgc                                   34
```

<210> SEQ ID NO 13
<211> LENGTH: 28
<212> TYPE: DNA

```
<213> ORGANISM: Artificial Sequence
<220> FEATURE:
<223> OTHER INFORMATION: primer hisG(G233H/T235Q)-AR

<400> SEQUENCE: 13
cgtgccagtg gggatacctg tgggtggg                                              28

<210> SEQ ID NO 14
<211> LENGTH: 30
<212> TYPE: DNA
<213> ORGANISM: Artificial Sequence
<220> FEATURE:
<223> OTHER INFORMATION: primer hisG(G233H/T235Q)-BF

<400> SEQUENCE: 14
aaccccaggc ctatcccacc cacaggtatc                                            30

<210> SEQ ID NO 15
<211> LENGTH: 33
<212> TYPE: DNA
<213> ORGANISM: Artificial Sequence
<220> FEATURE:
<223> OTHER INFORMATION: Primer hisG(G233H/T235Q)-BR

<400> SEQUENCE: 15
atgcctgcag gtcgacgcaa ggttggcaac aac                                        33

<210> SEQ ID NO 16
<211> LENGTH: 281
<212> TYPE: PRT
<213> ORGANISM: Corynebacterium glutamicum

<400> SEQUENCE: 16
```

| Met | Leu | Lys | Ile | Ala | Val | Pro | Asn | Lys | Gly | Ser | Leu | Ser | Glu | Arg | Ala |
|---|---|---|---|---|---|---|---|---|---|---|---|---|---|---|---|
| 1 | | | | 5 | | | | | 10 | | | | | 15 | |

| Met | Glu | Ile | Leu | Ala | Glu | Ala | Gly | Tyr | Ala | Gly | Arg | Gly | Asp | Ser | Lys |
|---|---|---|---|---|---|---|---|---|---|---|---|---|---|---|---|
| | | 20 | | | | | 25 | | | | | 30 | | | |

| Ser | Leu | Asn | Val | Phe | Asp | Glu | Ala | Asn | Asn | Val | Glu | Phe | Phe | Phe | Leu |
|---|---|---|---|---|---|---|---|---|---|---|---|---|---|---|---|
| | | 35 | | | | | 40 | | | | | 45 | | | |

| Arg | Pro | Lys | Asp | Ile | Ala | Ile | Tyr | Val | Ala | Gly | Gly | Gln | Leu | Asp | Leu |
|---|---|---|---|---|---|---|---|---|---|---|---|---|---|---|---|
| | 50 | | | | | 55 | | | | | 60 | | | | |

| Gly | Ile | Thr | Gly | Arg | Asp | Leu | Ala | Arg | Asp | Ser | Gln | Ala | Asp | Val | His |
|---|---|---|---|---|---|---|---|---|---|---|---|---|---|---|---|
| 65 | | | | | 70 | | | | | 75 | | | | | 80 |

| Glu | Val | Leu | Ser | Leu | Gly | Phe | Gly | Ser | Ser | Thr | Phe | Arg | Tyr | Ala | Ala |
|---|---|---|---|---|---|---|---|---|---|---|---|---|---|---|---|
| | | | 85 | | | | | 90 | | | | | 95 | | |

| Pro | Ala | Asp | Glu | Glu | Trp | Ser | Ile | Glu | Lys | Leu | Asp | Gly | Lys | Arg | Ile |
|---|---|---|---|---|---|---|---|---|---|---|---|---|---|---|---|
| | | | 100 | | | | | 105 | | | | | 110 | | |

| Ala | Thr | Ser | Tyr | Pro | Asn | Leu | Val | Arg | Asp | Asp | Leu | Ala | Ala | Arg | Gly |
|---|---|---|---|---|---|---|---|---|---|---|---|---|---|---|---|
| | | 115 | | | | | 120 | | | | | 125 | | | |

| Leu | Ser | Ala | Glu | Val | Leu | Arg | Leu | Asp | Gly | Ala | Val | Glu | Val | Ser | Ile |
|---|---|---|---|---|---|---|---|---|---|---|---|---|---|---|---|
| | 130 | | | | | 135 | | | | | 140 | | | | |

| Lys | Leu | Gly | Val | Ala | Asp | Ala | Ile | Ala | Asp | Val | Val | Ser | Thr | Gly | Arg |
|---|---|---|---|---|---|---|---|---|---|---|---|---|---|---|---|
| 145 | | | | | 150 | | | | | 155 | | | | | 160 |

| Thr | Leu | Arg | Gln | Gln | Gly | Leu | Ala | Pro | Phe | Gly | Glu | Val | Leu | Cys | Thr |
|---|---|---|---|---|---|---|---|---|---|---|---|---|---|---|---|
| | | | | 165 | | | | | 170 | | | | | 175 | |

| Ser | Glu | Ala | Val | Ile | Val | Gly | Arg | Lys | Asp | Glu | Lys | Val | Thr | Pro | Glu |
|---|---|---|---|---|---|---|---|---|---|---|---|---|---|---|---|
| | | | 180 | | | | | 185 | | | | | 190 | | |

| Gln | Gln | Ile | Leu | Leu | Arg | Arg | Ile | Gln | Gly | Ile | Leu | His | Ala | Gln | Asn |
|---|---|---|---|---|---|---|---|---|---|---|---|---|---|---|---|
| | | 195 | | | | | 200 | | | | | 205 | | | |

```
Phe Leu Met Leu Asp Tyr Asn Val Asp Arg Asp Asn Leu Asp Ala Ala
            210             215             220
Thr Ala Val Thr Pro Gly Leu Ser Gly Pro Thr Val Ser Pro Leu Ala
225             230             235             240
Arg Asp Asn Trp Val Ala Val Arg Ala Met Val Pro Arg Arg Ser Ala
                245             250             255
Asn Ala Ile Met Asp Lys Leu Ala Gly Leu Gly Ala Glu Ala Ile Leu
            260             265             270
Ala Ser Glu Ile Arg Ile Ala Arg Ile
            275             280
```

PROMOTER AND A METHOD FOR PRODUCING L-AMINO ACID USING THE SAME

STATEMENT REGARDING SEQUENCE LISTING

The Sequence Listing associated with this application is provided in text format in lieu of a paper copy, and is hereby incorporated by reference into the specification. The name of the text file containing the Sequence Listing is 200187_465USPC_SEQUENCE_LISTING.txt. The text file is 7 KB, was created on Feb. 10, 2020, and is being submitted electronically via EFS-Web.

TECHNICAL FIELD

The present disclosure relates to a novel promoter and a method for producing L-amino acid using the promoter, and more specifically, to a novel polynucleotide having promoter activity, a vector and a microorganism of the genus *Corynebacterium* comprising the polynucleotide, a method for producing L-amino acids and a fermented composition using the microorganism, and the fermented composition.

BACKGROUND ART

L-Amino acids are the basic building blocks of proteins and are used as important materials such as pharmaceutical raw materials, food additives, animal feeds, nutritional supplements, pesticides, bactericides, etc. Among these, L-glutamic acid is a representative amino acid produced by fermentation and has a unique, distinctive taste (umami taste), and thus is an important amino acid widely used in the food field as well as in the medical field and other animal feed fields. Further, glycine is mainly used as a flavor enhancer in the food industry because of its sweet taste, and is used with natural flavor enhancers to enhance taste. Furthermore, glycine is also used for its antioxidant activity, buffering action, etc., and in terms of medicine, it is used in infusion solutions, antacids, multi-amino acid preparations, and nutritional supplements.

A typical method for producing amino acids includes a fermentation method using a microorganism of the genus *Brevibacterium* or *Corynebacterium* (Amino Acid Fermentation, Gakkai Shuppan Center: 195-215, 1986) or using *Escherichia coli* or microorganisms of the genera *Bacillus, Streptomyces, Penicillum, Klebsiella, Erwinia, Pantoea*, etc. (U.S. Pat. Nos. 3,220,929 and 6,682,912). In addition, such amino acids are also produced by an industrial method using a synthetic process such as the monochloroacetic acid method, the Strecker method, or the like.

Additionally, various studies have been conducted for efficiently producing amino acids; for example, efforts have been made to develop microorganisms or fermentation process technologies for producing amino acids with high efficiency. Particularly, approaching methods for specific to target materials have been developed, such as enhancement of expression of genes encoding enzymes involved in the biosynthesis of the amino acids in the strain of the genus *Corynebacterium* or deletion of genes unnecessary for the biosynthesis of amino acids (Korean Patent Nos. 10-0924065 and 1208480). In addition to these methods, a method for removing genes that are not involved in the production of amino acids and a method for removing genes whose functions for producing amino acids are not specifically known have also been utilized. However, there is still a growing need to study methods for efficiently producing amino acids with high yield.

DISCLOSURE

Technical Problem

The present inventors have made efforts to develop a method capable of simultaneously producing several amino acids, and as a result, they have developed a novel polynucleotide having the promoter activity of the present disclosure, and have found that the novel polynucleotide can improve glycine productivity while maintaining the glutamic acid productivity of the strain, thereby completing the present disclosure.

Technical Solution

An objective of the present disclosure is to provide a polynucleotide having promoter activity, wherein, in the nucleotide sequence of SEQ ID NO: 1, the $53^{rd}$ and $55^{th}$ nucleotides are substituted with T; or the $53^{rd}$ and $55^{th}$ nucleotides are substituted with T and the $60^{th}$ nucleotide is substituted with G.

Another objective of the present disclosure is to provide a vector comprising the polynucleotide; and a gene encoding a target protein operably linked to the polynucleotide.

Still another objective of the present disclosure is to provide a microorganism of the genus *Corynebacterium* comprising the polynucleotide; and a gene encoding a target protein operably linked to the polynucleotide.

Still another objective of the present disclosure is to provide a method for producing a target substance, comprising: culturing the microorganism of the genus *Corynebacterium* in a medium; and recovering a target substance from the medium.

Still another objective of the present disclosure is to provide a method for preparing a fermented composition, comprising fermenting by culturing the microorganism of the genus *Corynebacterium* in a medium.

Still another objective of the present disclosure is to provide a fermented composition prepared by the above method.

Advantageous Effects

The novel promoter of the present disclosure is introduced into a microorganism producing amino acids to increase the production amounts of the amino acids in the microorganisms. In particular, in the case of producing the amino acids by using the novel promoter, glycine, which has been prepared by an existing synthetic method, can be produced by a fermentation method, and further, glutamic acid and glycine can be produced simultaneously. Therefore, the novel promoter can be useful for the production of the amino acids. In addition, the present disclosure can improve the taste and palatability of a fermented product by regulating the amounts of glutamic acid and glycine in the fermented product for the preparation of a fermented broth and its application in seasoning products.

BEST MODE

Hereinbelow, the present disclosure will be described in detail. Meanwhile, each description and embodiment disclosed in the present disclosure may be applied to other descriptions and embodiments. That is, all combinations of various elements disclosed in the present disclosure fall within the scope of the present disclosure. Further, the specific descriptions disclosed below should not be construed as limiting the scope of the present disclosure.

To achieve the objectives above, an aspect of the present disclosure provides a polynucleotide having promoter activity, wherein, in the nucleotide sequence of SEQ ID NO: 1, the $53^{rd}$ and $55^{th}$ nucleotides are substituted with T; or the $53^{rd}$ and $55^{th}$ nucleotides are substituted with T and the $60^{th}$ nucleotide is substituted with G.

As used herein, the term "nucleotide sequence of SEQ ID NO: 1" may refer to a part of the promoter sequence of the phosphoribosyl-ATP pyrophosphatase (HisE) gene.

In particular, the term "phosphoribosyl-ATP pyrophosphatase" refers to an enzyme involved in the histidine synthesis pathway, in which L-histidine is synthesized from 5-phospho-alpha-D-ribose 1-diphosphate, and may interchangeably be referred to as "HisE" in the present disclosure. The histidine synthesis pathway consists of a total of nine steps relating nine enzymes respectively (HisG-HisE-HisI-HisA-HisH-HisB-HisC-HisN-HisD), wherein the HisE relates to the second step after ATP phosphoribosyltransferase (HisG), which relates to the first step.

As used herein, the term "promoter" refers to a sequence of a non-translated nucleotide upstream of a coding region, which includes a polymerase-binding domain and has a transcription initiation activity for a target gene of the promoter into mRNA, that is, a DNA domain to which a polymerase binds to initiate the transcription of a gene, and may be located at the 5'-region of the initiation area of mRNA transcription. In particular, the target gene of the promoter may be a gene encoding phosphoribosyl-ATP pyrophosphatase, but is not limited thereto.

In the present disclosure, the polynucleotide having the activity of a promoter including the polynucleotide sequence consist of SEQ ID NO: 2 or 3 may be interchangeably referred to by the terms "the polynucleotide", "the nucleotide sequence of the present disclosure", "polynucleotide of the present disclosure", "hisEG promoter", etc. In addition, these terms may be used in the present disclosure.

The polynucleotide of the present disclosure is one in which a nucleotide sequence of SEQ ID NO: 1, i.e., a promoter sequence of the gene hisEG, is modified, and specifically, such modification may be one in which, in nucleotide sequence of SEQ ID NO: 1, the $53^{rd}$ and $55^{th}$ nucleotides are substituted with T; or the $53^{rd}$ and $55^{th}$ nucleotides are substituted with T and the $60^{th}$ nucleotide is substituted with G. Accordingly, the polynucleotide may be one consisting of the nucleotide sequence of SEQ ID NO: 2 or 3.

In particular, the term "modification" refers to a phenotypic change that is genetically or non-genetically stable, and may be interchangeably referred to by the term "mutation" in the present disclosure.

Specifically, the polynucleotide may have promoter activity that is modified (increased or decreased) relative to the activity of a polynucleotide, which does not include the polynucleotide modification. Accordingly, the expression of a target gene operably linked to the polynucleotide and the activity of a protein encoded by the target gene may be regulated (increased or decreased), and further, the expression of genes other than the target gene may be regulated.

For the objectives of the present disclosure, the polynucleotide may be one for enhancing the expression of hisE gene. Additionally, the genes, hisE and hisG, consist of operons, and thus the polynucleotide may further have a purpose for enhancing the expression of the gene hisG.

Additionally, the polynucleotide may be one for increasing the production amount of glycine.

In particular, the term "HisG" as used herein refers to "ATP phosphoribosyltransferase", and is an enzyme involved in the histidine synthesis pathway. The histidine synthesis pathway consists of a total of nine enzymes (HisG-HisE-HisI-HisA-HisH-HisB-HisC-HisN-HisD), wherein the HisG constitutes the first step.

Accordingly, the genes, hisE and hisG, consist of operons, and thus the polynucleotide of the present disclosure can regulate the transcription of the gene hisE as well as the gene hisG. Therefore, the target gene may be a gene encoding ATP phosphoribosyltransferase phosphoribosyl-ATP pyrophosphatase (HisE), a gene encoding ATP phosphoribosyltransferase (HisG), or a combination thereof.

It has been known that the HisE and HisG are involved in the production of histidine, but the relationship thereof with the production of glycine is not known and was first identified by the present inventors. In particular, the present inventors have confirmed for the first time the increase in the activity of HisE and HisG enzymes due to the overexpression of hisE and/or hisG by the modification of the promoter of the gene hisEG, as well as the effects of increasing and maintaining the production amount of glycine due to the same.

Herein, the term "L-glutamic acid" or "L-glutamate" refers to a kind of an amino acid and is classified as a non-essential amino acid. L-Glutamic acid is known to be the most common excitatory neurotransmitter in the central nervous system. In addition, since L-glutamic acid has an umami taste, the monosodium glutamate (MSG) has been developed therefrom and is widely used as a flavor enhancer. It is generally produced through fermentation of microorganisms producing glutamic acid.

Additionally, the term "glycine" refers to an amino acid having a colorless crystalline form and a sweet taste. Glycine is mainly used as a flavor enhancer for foods, and in terms of medicine, it is used in infusion solutions, antacids, multi-amino acid preparations, and nutritional supplements. In general, glycine is prepared by an industrial synthetic method such as the monochloroacetic acid method, the Strecker method, or the like. However, there is an inconvenience in that since a mixture of D-type and L-type amino acids are produced when using the synthetic method, it is necessary to perform optical resolution. Therefore, it is required to prepare glycine by a fermentation method which has various advantages, i.e., the reaction conditions are moderate, mass production is possible in a short period of time, the process is environmentally friendly, and the produced material is biodegradable.

Specifically, the polynucleotide may be one composed of the nucleotide sequence of SEQ ID NO: 2 or 3.

Additionally, the nucleotide sequence of the present disclosure may be modified by known mutagenesis methods, such as directed evolution, site-directed mutagenesis, etc.

Therefore, the polynucleotide may comprise a polynucleotide including the nucleotide sequence that has a homology to the nucleotide sequence of SEQ ID NO: 2 or 3 of at least 60%, specifically at least 70%, more specifically at least 80%, and even more specifically at least 83%, 84%, 88%, 90%, 93%, 95%, or 97%. It is apparent that a polynucleotide sequence having such homology, a part of which is deleted, modified, substituted, or added, is also within the scope of the present disclosure, as long as the resulting polynucleotide sequence has a biological activity substantially equivalent or corresponding to the nucleotide sequence of SEQ ID NO: 2 or 3.

As used herein, the term "homology" may indicate the degree of matching with the given nucleotide sequence, and may be presented as a percentage (%). In the present disclosure, a homology sequence having an activity which is identical or similar to the given nucleotide sequence is presented as "% homology". The homology to the nucleotide sequence can be determined by, for example, algorithm BLAST (see Karlin and Altschul, Pro. Natl. Acad. Sci. USA, 90, 5873(1993) or FASTA (see Pearson, Methods Enzymol., 183, 63, 1990). Based on this algorithm, programs called BLASTN or BLASTX have been developed (see http://www.ncbi.nlm.nih.gov).

As used herein, the term "stringent conditions" refers to conditions which permit specific hybridization between polynucleotides. For example, such stringent conditions are specifically described in the literature (e.g., J. Sambrook et al). For example, the stringent conditions may include conditions in which genes having a high homology (e.g., 60% or more, specifically 90% or more, more specifically 95% or more, even more specifically 97% or more, and even more specifically 99% or more) can hybridize with each other, whereas genes having a lower homology thereof cannot hybridize with each other; or conditions for conventional southern hybridization (i.e., conditions for washing once, and specifically two or three times at a salt concentration and temperature corresponding to 60° C., 1×SSC, 0.1% SDS, specifically at 60° C., 0.1×SSC, 0.1% SDS; and more specifically at 68° C., 0.1×SSC, 0.1% SDS). Hybridization requires that two nucleotides have complementary sequences, although mismatches between bases are possible depending on the severity of hybridization. The term "complementary" is used to describe the relationship between nucleotide bases that are capable of being hybridized with each other. For example, with respect to DNA, adenosine is complementary to thymine and cytosine is complementary to guanine. Therefore, the present disclosure may also include substantially similar nucleotide sequences as well as isolated polynucleotide fragments complementary to the entire sequence.

Specifically, the polynucleotide having homology can be detected using hybridization conditions including a hybridization step at a $T_m$ value of 55° C. and using the above-described conditions. In addition, the $T_m$ value may be 60° C., 63° C., or 65° C., but is not limited thereto. One of ordinary skill in the art can appropriately adjust the $T_m$ value according to its purpose. The appropriate stringency of hybridizing the polynucleotides is dependent on the length and degree of complementarity of the polynucleotides, and the variables are well known in the art (see Sambrook et al., supra, 9.50-9.51, 11.7-11.8).

In particular, the expression "consist of the nucleotide sequence of SEQ ID NO: 2 or 3" means that, as when using a restriction enzyme, the addition, deletion, and/or mutation of a nucleotide is not excluded, which may occur during the process of linking to a target gene when the polynucleotide is ligated to the target gene and used as a promoter.

For example, the polynucleotide having the activity of a promoter consisting of the nucleotide sequence of SEQ ID NO: 2 or 3 can be included without limitation if it includes the nucleotide sequence which has the promoter activity of the present disclosure and which is hybridized under stringent conditions with a complementary sequence to all or a part of the nucleotide sequence of SEQ ID NO: 2 or 3.

Furthermore, the polynucleotide of the present disclosure may be operably linked to a gene encoding a target protein.

As used herein, the term "gene expression regulatory sequence" refers to a sequence which includes the polynucleotide of the present disclosure and is capable of expressing a target gene operably linked to the polynucleotide.

One of ordinary skill in the art may be able to attempt to enhance the expression of the target gene by modifying the gene regulatory sequence including a promoter, for example, the enhancement of gene expression by the modification of an initiation codon. In an embodiment, the modification may be a substitution of the initiation codon from 'GTG' to 'ATG'.

As used herein, the term "operably linked" means that the polynucleotide of the present disclosure having promoter activity is functionally linked to the gene sequence to initiate and mediate transcription of a target gene. Operable linking with the gene sequence can be achieved using a gene recombinant technique known in the art, and site-specific DNA cleavage and ligation can be performed by using a restriction enzyme and ligase known in the art, but these are not limited thereto.

Furthermore, the gene expression regulatory sequence of the present disclosure may further include any operator sequence for regulating transcription of genes in addition to promoters for performing the transcription of genes, as well as a sequence encoding a suitable mRNA ribosome binding site, DNA for regulating the termination of transcription and translation, etc.

For example, a regulatory sequence suitable for prokaryotes may further include ribosome binding sites in addition to promoters, but is not limited thereto. The polynucleotide of the present disclosure having promoter activity may consist of a sequence for regulating the gene expression as described above, as required by one of ordinary skill in the art.

In the present disclosure, the target gene refers to a gene encoding a target protein whose expression is to be regulated in a microorganism.

For example, the gene may be a gene involved in the production of amino acids such as glutamic acid, glycine, histidine, etc., but is not limited thereto. Specifically, the gene may be a gene encoding a histidine biosynthesis-related enzyme, but is not limited thereto. More specifically, the gene may be a gene encoding HisE and/or HisG, but is not limited thereto. For example, the hisE gene and hisG gene may constitute an operon and the polynucleotide of the present disclosure can enhance the transcriptional activity of the hisE and/or hisG. Additionally, the hisE and hisG may be endogenous genes or foreign genes, and may include mutations for regulating their activities. For example, the HisG may include histidine feedback inhibition release mutation. The sequence of the gene encoding the HisE or HisG can be easily obtained by one of ordinary skill in the art through a known database such as GenBank of the National Institutes of Health (NIH).

For the objectives of the present disclosure, the gene expression regulatory sequence may increase the expression of the genes encoding the enzymes involved in the histidine synthesis, and specifically may increase the expression of hisE gene and/or hisG gene.

Still another aspect of the present disclosure provides a vector comprising the polynucleotide; and a gene encoding a target protein operably linked to the polynucleotide the gene expression regulatory sequence and a vector comprising the gene encoding a target protein.

The polynucleotide is as described above.

Specifically, the target protein may be phosphoribosyl-ATP pyrophosphatase (HisE), ATP phosphoribosyltransferase (HisG), or a combination thereof. As the target proteins, HisE and HisG may include a protein having a homology thereto, and may be those in which part of the amino acid(s) is(are) modified. In an embodiment, ATP phosphoribosyltransferase (HisG) may be one in which the $233^{rd}$ and $235^{th}$ amino acids of the HisG amino acid sequence of SEQ ID NO: 16 are substituted with histidine (H) and glutamine (Q), respectively.

As used herein, the term "vector" refers to an artificial DNA molecule having a genetic material capable of expressing a target gene in a suitable host, and refers to a DNA construct including the polynucleotide or a suitable gene expression regulatory sequence and a nucleotide sequence of the gene encoding a target protein operably linked to the regulatory sequence.

The vector used in the present disclosure is not particularly limited as long as it can be expressed in a host cell, and any vector known in the art may be used to transform the host cell. Examples of the conventional vector may include natural or recombinant plasmids, cosmids, viruses, and bacteriophages.

For example, as a phage vector or cosmid vector, pWE15, M13, λLB3, λBL4, λIXII, λASHII, λAPII, λt10, λt11, Charon4A, Charon21A, etc. may be used; and as a plasmid vector, those based on pBR, pUC, pBluescriptII, pGEM, pTZ, pCL, pET, etc. may be used.

Additionally, an endogenous promoter in the chromosome may be replaced with the polynucleotide of the present disclosure having promoter activity via the vector for chromosomal insertion in the host cell. For example, vectors pECCG117, pDZ, pACYC177, pACYC184, pCL, pUC19, pBR322, pMW118, pCC1BAC, pCES208, pXMJ19, etc. may be used, but these are not limited thereto.

Additionally, the insertion of the polynucleotide into the chromosome may be accomplished by any method known in the art, e.g., by homologous recombination.

Since the vector of the present disclosure can be inserted into the chromosome by inducing a homologous recombination, the selection marker may be additionally included to confirm a successful gene insertion into the chromosome. A selection marker is for screening the cells which are transformed with the vector, in other words, for determining whether the polynucleotide is inserted. The markers that provide selectable phenotypes such as drug resistance, auxotrophy, resistance to toxic agents, or expression of surface proteins may be used. In an environment treated with a selective agent, only the cells expressing the selection marker can survive, or the cells show a different phenotype, and thus the successfully transformed cells can be selected through this method.

As used herein, the term "transformation" refers to the introduction of the vector comprising the polynucleotide or the gene expression regulatory sequence and the gene encoding a target protein into the host cell in order to allow the expression of the gene in the host cell. Furthermore, as long as the target gene can be expressed in the host cell, it does not matter whether the transformed polynucleotide and the transformed gene encoding the target gene are located on the chromosome of the host cell or outside of the chromosome, and both cases are included.

The transformation method may include all methods of introducing the gene expression regulatory sequence and the gene encoding a target protein into the cell, and may be carried out by selecting a suitable standard technique known in the art depending on the host cell. For example, a suitable standard technique may be selected among electroporation, calcium phosphate ($CaPO_4$) precipitation, calcium chloride ($CaCl_2$) precipitation, microinjection, a polyethyleneglycol (PEG) technique, a DEAE-dextran technique, a cationic liposome technique, and a lithium acetate-DMSO technique, but is not limited thereto.

Still another aspect of the present disclosure provides a microorganism of the genus *Corynebacterium* comprising the polynucleotide; and a gene encoding a target gene operably linked to the polynucleotide.

The polynucleotide and gene encoding a target gene operably linked to the polynucleotide are as described above.

As used herein, the term "microorganism" includes all of a wild-type microorganism and a naturally or artificially genetically modified microorganism, and it may be a microorganism having a particular attenuated or reinforced mechanism due to insertion of a foreign gene or reinforcement or attenuation of activity of an endogenous gene.

In the present disclosure, the microorganism may include the polynucleotide, specifically the polynucleotide and/or a gene encoding a target gene operably linked to the polynucleotide. Alternatively, the microorganism may include the polynucleotide or the gene expression regulatory sequence, and the vector including the polynucleotide or the gene expression regulatory sequence and the gene encoding a target protein, but is not limited thereto. In addition, the polynucleotide, the gene encoding the target protein, and the vector may be introduced into the microorganism by transformation, but are not limited thereto. Furthermore, as long as the gene can be expressed in the microorganism, it does not matter whether the polynucleotide and the gene encoding a target protein are located on the chromosome or outside of the chromosome.

For the objectives of the present disclosure, the microorganism including the polynucleotide and the gene encoding a target protein may be one in which the production amount of glutamic acid is maintained and the production amount of glycine is increased.

For example, the microorganism may be one in which the activity of HisE and/or HisG is enhanced.

In the present disclosure, the microorganism may be included without limitation as long as it is a microorganism in which the polynucleotide of the present disclosure having promoter activity is introduced so that it operates as a promoter.

Specifically, the microorganism may be a microorganism of the genus *Corynebacterium*; more specifically may be *Corynebacterium glutamicum* or *Corynebacterium flavum*; and most specifically may be *Corynebacterium glutamicum*, but is not limited thereto.

Still another aspect of the present disclosure provides a method for producing a target substance, comprising: culturing the microorganism of the genus *Corynebacterium* in a medium; and recovering a target substance from the medium.

The polynucleotide and microorganism are as described above.

In the present disclosure, the target substance may be an amino acid. Specifically, the amino acid may be an L-type amino acid unless otherwise stated, and may be an amino acid selected from the group consisting of glycine, alanine, valine, leucine, isoleucine, threonine, serine, cysteine, glutamine, methionine, aspartate, asparagine, glutamic acid, lysine, arginine, histidine, phenylalanine, tyrosine, tryptophan, proline, and a combination thereof, but is not limited thereto.

More specifically, the amino acid may be glutamic acid, glycine, or a combination thereof, but is not limited thereto.

As used herein, the term "culture" refers to culturing of a microorganism under artificially controlled environmental conditions. In the present disclosure, the method for producing a target substance using a microorganism with the polynucleotide may be carried out by a method widely known in the art. Specifically, the culture may be carried out in a batch process or in a continuous process such as a fed-batch process or a repeated fed-batch process, but is not limited thereto. The medium used for the culture must satisfy the requirements of a particular strain employed. The culture medium suitable for used in culturing the Corynebacterium strain is known in the art (e.g., Manual of Methods for General Bacteriology by the American Society for Bacteriology, Washington D.C., USA, 1981).

Carbon sources that can be used in the culture medium may be saccharides and carbohydrates such as glucose., sucrose, lactose, fructose, maltose, starch, and cellulose; oils and lipids such as soybean oil, sunflower seed oil, peanut oil, and coconut oil; fatty acids such as palmitic acid, steric acid, linoleic acid; alcohols such as glycerol and ethanol; and organic acids such as acetic acid. These materials may be used separately or in combination, but are not limited thereto.

Examples of nitrogen sources that can be used include peptone, yeast extract, broth, malt extract, corn steep liquor, soybean meal and urea, or inorganic compounds such as ammonium sulfate, ammonium chloride, ammonium phosphate, ammonium carbonate, and ammonium nitrate. These nitrogen sources may also be used separately or in combination, but are not limited thereto.

Phosphorous sources that can be used in the culture medium may include dipotassium hydrogen phosphate, potassium di hydrogen phosphate, or corresponding sodium-containing salts. In addition, the culture medium may contain metal salts essential to the growth of cells, and may be supplemented with materials essential for the growth, such as amino acids and vitamins, in addition to the materials above. Further, precursors suitable for the culture medium may be used. The above raw substances may be adequately fed into the culture in a batch or continuous manner.

During the culture of the microorganism, the pH of the culture may be adjusted by a proper basic compound such as sodium hydroxide, potassium hydroxide, or ammonia, or an acidic compound such as phosphoric acid or sulfuric acid. Foaming may be adjusted by an anti-foaming agent such as a fatty acid polyglycol ester. The aerobic condition of the culture may be maintained by introducing oxygen or oxygen-containing gas mixtures (e.g., air).

The temperature of the culture (medium) may be generally 20° C. to 45° C., specifically 25° C. to 40° C. Culturing may be continued until the desired production amount of the target substance is obtained, specifically for 10 hours to 160 hours.

The recovery of the target substance from the culture (medium) may be carried out by a conventional separation method known in the art. For the separation method, methods such as centrifugation, filtration, chromatography, crystallization, etc. may be used. For example, a supernatant obtained by centrifuging the culture medium at a low speed to remove biomass may be separated by ion-exchange chromatography, but is not limited thereto. In an alternative method, the target substance may be recovered without an additional purification process, by performing processes of separation and filtration of bacterial cells from a culture product (medium). In another alternative method, the target substance may be recovered, and the recovery step may further include a purification process.

Still another aspect of the present disclosure provides a method for preparing a fermented composition, comprising fermenting by culturing the microorganism of the genus Corynebacterium in a medium.

Still another aspect of the present disclosure provides a fermented composition prepared by the above method.

The polynucleotide and microorganism are as described above, and the step of culturing the microorganism in a medium is also as described above.

As used herein, the term "the fermented composition" refers to a composition obtained by culturing the microorganism of the present disclosure in a medium. Furthermore, the fermented composition may include a composition in the form of a liquid or powder obtained after culturing the microorganism followed by a suitable post-treatment. In particular, the suitable post-treatment process may include, for example, a process of culturing a microorganism, a process of removing bacterial cells, a concentration process, a filtration process, and a process of mixing carriers, and may further include a drying process. In some cases, the post-treatment process may not include a purification process. The fermented composition, obtained by culturing the microorganism of the present disclosure, is characterized in that the amount of glutamic acid production is increased while the amount of lactic acid production is reduced, thereby making it possible to provide an optimum taste.

Additionally, "the fermented composition" does not exclude seasoning products (e.g., powdered soup products, snack seasoning products, etc.) containing the composition in the form of a liquid or powder. Furthermore, the "fermented composition" does not exclude cases in which a substance obtained by a non-fermentation process or another substance obtained by a non-natural process is further included, as long as the composition obtained by culturing the microorganism of the present disclosure is contained therein.

MODE FOR INVENTION

Hereinbelow, the present disclosure will be described in detail with accompanying exemplary embodiments. However, the exemplary embodiments disclosed herein are only for illustrative purposes and should not be construed as limiting the scope of the present disclosure.

EXAMPLE 1

Selection of Mutant Strain for Increasing Glycine Productivity

EXAMPLE 1-1

Induction of Random Mutation by UV Irradiation

In order to select mutant strains with improved glycine productivity, i.e., target products of fermentation, wild-type Corynebacterium glutamicum (ATCC13869) was plated on nutrient media containing agar and cultured at 30° C. for 16 hours. Hundreds of the thus-obtained colonies were irradiated with UV at room temperature to induce a random mutation on the genome in the strain.

EXAMPLE 1-2

Experiment on Fermentation Titer of Mutation-Inducing Strain and Selection of Strain Thereafter, the experiment on fermentation titer of the mutant strains, in which the random mutation had been induced, was carried out.

Each colony was subcultured in the nutrient media, and then cultured in fermentation media for 5 hours. Thereafter, 25% tween 40 was added to each medium at a concentration of 0.4%, and then each colony was cultured again for 32 hours.

Nutrient Medium:

Glucose 1%, meat juice 0.5%, polypeptone 1%, sodium chloride 0.25%, yeast extract 0.5%, agar 2%, urea 0.2%, pH 7.2

Fermentation Medium:

Raw sugar 6%, calcium carbonate 5%, ammonium sulfate 2.25%, potassium monophosphate 0.1%, magnesium sulfate 0.04%, iron sulfate (10 mg/L), biotin (0.3 mg/L), thiamine hydrochloride (0.2 mg/L)

Each of the colonies was cultured under the conditions above, and then mutant strains producing L-glutamic acid, the produced amount of which is equal to or greater than that produced by wild-type *Corynebacterium glutamicum* (ATCC13869), were selected. In addition, with respect to the selected mutant strains, the concentration of L-glutamic acid was measured by YSI, and the concentration of glycine was measured by HPLC. The measured concentrations of L-glutamic acid and glycine are shown in Table 1.

TABLE 1

| Strain | L-Glutamic acid (g/L) | L-Glycine (mg/L) |
| --- | --- | --- |
| ATCC13869 | 14.0 | 119 |
| ATCC13869-g1 | 13.2 | 102 |
| ATCC13869-g2 | 9.6 | 35 |
| ATCC13869-g3 | 13.9 | 121 |
| ATCC13869-g4 | 13.3 | 110 |
| ATCC13869-g5 | 12.7 | 101 |
| ATCC13869-g6 | 14.8 | 132 |
| ATCC13869-g7 | 2.1 | 7 |
| ATCC13869-g8 | 8.4 | 75 |
| ATCC13869-g9 | 13.5 | 115 |
| ATCC13869-g10 | 14.2 | 143 |
| ATCC13869-g11 | 12.6 | 108 |
| ATCC13869-g12 | 13.7 | 103 |
| ATCC13869-g13 | 10.1 | 82 |
| ATCC13869-g14 | 14.2 | 105 |
| ATCC13869-g15 | 13.5 | 100 |
| ATCC13869-g16 | 7.2 | 67 |
| ATCC13869-g17 | 12.8 | 101 |
| ATCC13869-g18 | 13.0 | 99 |
| ATCC13869-g19 | 11.9 | 82 |
| ATCC13869-g20 | 14.0 | 152 |
| ATCC13869-g21 | 13.8 | 111 |
| ATCC13869-g22 | 9.7 | 120 |
| ATCC13869-g23 | 13.2 | 114 |
| ATCC13869-g24 | 13.3 | 114 |

Based on Table 1, "ATCC13869-g3", "ATCC13869-g6", "ATCC13869-g10", "ATCC13869-g10", and "ATCC13869-g20" were selected as the strains in which the amount of glutamic acid produced was equal or greater and the amount of glycine produced was increased compared to those produced in the wild-type strain.

EXAMPLE 2

Confirmation of Mutation Through Gene Sequencing

In order to confirm the gene mutation of the mutant strains, genes in the strains ATCC13869-g3, ATCC13869-g6, ATCC13869-g10, and ATCC13869-g20 were sequenced and compared with those of the wild-type strain.

As a result, it was found that the strains ATCC13869-g3 and ATCC13869-g10 contained the same mutation at a specific position in the promoter region of a gene encoding phosphoribosyl-ATP pyrophosphatase (HisE). Additionally, it was found that the ATCC13869-g20 strain contained an additional mutation, in addition to the same mutation, at a specific position in the promoter region of a gene encoding HisE of ATCC13869-g3 and ATCC13869-g10 strains.

Specifically, it was confirmed that the strains ATCC13869-g3 and ATCC13869-g10 contained mutations in which the $53^{rd}$ and $55^{th}$ nucleotides, A and G, in the sequence of the promoter region of SEQ ID NO: 1 are substituted with T. It was confirmed that the ATCC13869-g20 strain contained a mutation in which, in the nucleotide sequence of the promoter region of SEQ ID NO: 1, the $53^{rd}$ nucleotide (i.e., A) was substituted with T and the $55^{th}$ nucleotide (i.e., G) was substituted with T and the $60^{th}$ nucleotide (i.e., T) was substituted with G. The promoter region of SEQ ID NO: 1 was a sequence commonly included in a microorganism of the genus *Corynebacterium*, more specifically, the wild-type *Corynebacterium glutamicum* (ATCC13032, ATCC13869, and ATCC14067).

Therefore, in Examples 3 and 4, attempts were made to confirm whether the mutation above affected the production amounts of glutamic acid and glycine in the microorganism of the genus *Corynebacterium*.

EXAMPLE 3

Preparation of Strain Introduced with Mutation and Confirmation of Production Amount of Glycine

EXAMPLE 3-1

Preparation of Strain Introduced with Mutation

Preparation of a mutant strain introduced with the mutation confirmed in Example 2 was attempted. Specifically, in order to introduce the mutation into the wild-type *Corynebacterium glutamicum* ATCC13869 (i.e., in order to substitute the $53^{rd}$ and $55^{th}$ nucleotides of the polynucleotide sequence of SEQ ID NO: 1 with T; or to substitute the $53^{rd}$ and $55^{th}$ nucleotides of the polynucleotide sequence of SEQ ID NO: 1 with T and the $60^{th}$ nucleotide of the polynucleotide sequence of SEQ ID NO: 1 with G), the oligonucleotide in a reverse direction, which contains a target mutation, was designed with a 75-mer length (SEQ ID NO: 4 or 5).

Specifically, the oligonucleotide (30 μg) of SEQ ID NO: 4 or 5 was transformed into the wild-type *Corynebacterium glutamicum* strains ATCC13869 and ATCC13032 using an electric pulse method (Appl. Microbiol. Biotechnol., 1999, 52: 541-545), and then a complex liquid medium (1 mL) was added thereto. The resultants were then cultured at 30° C. for 30 minutes while shaking at 160 rpm. Thereafter, the culture medium was incubated on ice for 10 minutes, centrifuged at 4000 rpm at 4° C. for 10 minutes, and then the supernatant was removed to obtain microbial cells. Thereafter, a 10% glycerol solution (4° C.) was added thereto and mixed, and then the results were centrifuged at 4000 rpm at 4° C. for 10 minutes. The supernatant was removed and then the microbial cells were washed. Such procedure was repeated once more to wash the microbial cells again, and a 10% glycerol solution (4° C. and 0.1 mL) was added thereto to prepare the strains for the next transformation. Thereafter, the process for the transformation was repeated 10 times with the oligonucleotide of SEQ ID NO: 4 or 5 using the electric pulse method described above, and then the resultants were plated on a complex plate medium to obtain colonies (Nat. Protoc., 2014 October; 9(10): 2301-16).

As a result of carrying out the analysis of the gene sequence of the obtained colonies, it was confirmed that the target mutation was introduced into the strains. In addition, the strains into which the mutation was introduced were named as "ATCC13869::hisEG-pro-2mt", "ATCC 13869::hisEG-pro-3mt" and "ATCC 13032::hisEG-pro-2mt", "ATCC13032::hisEG-pro-3mt".

EXAMPLE 3-2

Confirmation of Production Amount of Glycine

The mutant strains ATCC13869::hisEG-pro-2mt, ATCC13869::hisEG-pro-3mt, and ATCC13032::hisEG-pro-2mt, ATCC13032::hisEG-pro-3mt, which were prepared in Example 3-1, and their wild-type Corynebacterium glutamicum strains ATCC13869 and ATCC13032 were cultured in the same manner as in Example 1-2.

After the cultivation was completed, the concentrations of L-glutamic acid and glycine in each medium were measured. The measured concentrations of L-glutamic acid and glycine are shown in Table 2 below.

TABLE 2

| Strain | L-Glutamic acid (g/L) | L-Glycine (mg/L) |
|---|---|---|
| ATCC13869 | 14.2 | 122 |
| ATCC13869::hisEG-pro-2mt | 14.0 | 134 |
| ATCC13869::hisEG-pro-3mt | 14.3 | 141 |
| ATCC13032 | 9.1 | 73 |
| ATCC13032::hisEG-pro-2mt | 9.4 | 91 |
| ATCC13032::hisEG-pro-3mt | 9.3 | 99 |

As shown in Table 2, it was confirmed that the concentration of L-glutamic acid produced by each of the Corynebacterium glutamicum strains ATCC13869::hisEG-pro-2mt, ATCC 13869::hisEG-pro-3mt and ATCC 13032::hisEG-pro-2mt, ATCC 13032::hisEG-pro-3mt, into which the mutation was introduced, was similar to that produced by each of the wild-type Corynebacterium glutamicum strains ATCC 13869 and ATCC 13032.

On the contrary, the wild-type Corynebacterium glutamicum strains ATCC13869 and ATCC13032 produced 122 mg/L and 73 mg/L of glycine, respectively. However, the strains ATCC 13869::hisEG-pro-2mt and ATCC 13032::hisEG-pro-2mt produced 134 mg/L and 91 mg/L of glycine, respectively. Therefore, it was confirmed that the concentrations of glycine produced in the mutant strains were higher than those produced in the wild-type strains. Additionally, the strains ATCC13869::hisEG-pro-3mt and ATCC13032::hisEG-pro-3mt produced glycine 141 mg/L and 99 mg/L of glycine, respectively, thus showing higher concentrations of glycine than those produced in the strains ATCC13869::hisEG-pro-2mt and ATCC 13032::hisEG-pro-2mt.

That is, it was confirmed that the mutations remarkably increased the glycine productivity while maintaining the L-glutamic acid productivity in the microorganisms with no significant effect thereon.

Meanwhile, the strains ATCC13869::hisEG-pro-2mt and ATCC13869::hisEG-pro-3mt were deposited at the Korea Culture Center of Microorganisms (KCCM), which is an international depositary authority under the Budapest Treaty, on Feb. 28, 2018 and Mar. 14, 2019, under the strain name of "CA02-9206" and "CA02-9215", and was assigned Accession Nos. KCCM12226P and KCCM12457P.

EXAMPLE 4

Confirmation of Production Amounts of Glutamic Acid and Glycine of KFCC11074 into which Mutation is Introduced

EXAMPLE 4-1

Preparation of Vector into which Mutation is Introduced

In order to confirm whether the mutation exhibits the same effects even in the strains with the improved productivity of glutamic acid, in addition to the wild-type strains, attempts were made to introduce the mutation into the strain KFCC11074 (Korean Patent No. 10-0292299), which is known as a glutamic acid-producing strain.

Specifically, a vector for gene substitution was constructed in order to substitute the $53^{rd}$ and $55^{th}$ nucleotides of the polynucleotide sequence of SEQ ID NO: 1, which are contained in the strain, with T; and to substitute the $53^{rd}$ and $55^{th}$ nucleotides of the polynucleotide sequence of SEQ ID NO: 1 with T and the $60^{th}$ nucleotide of the polynucleotide sequence of SEQ ID NO: 1 with G. The gene fragments for constructing the vector were obtained by PCR using ATCC13869 genomic DNA as a template. Based on information on genes and adjacent nucleotide sequences of the Corynebacterium glutamicum (ATCC13869) registered in the National Institutes of Health GenBank (NIH GenBank), primers including the polynucleotides of SEQ ID NOS: 6, 7, 8, 9, 10 and 11 were prepared.

After denaturation at 95° C. for 5 minutes, PCR was carried out for a total of 30 cycles under the following conditions: denaturation at 95° C. for 30 seconds, annealing at 55° C. for 30 seconds, and polymerization at 72° C. for 1 minute. Thereafter, the polymerization reaction was carried out at 72° C. for 5 minutes. More specifically, the polynucleotide (500 bp) amplified using the primers of SEQ ID NOS: 6 and 7 and the polynucleotide (500 bp) amplified using the primers of SEQ ID NOS: 8 and 9 were obtained. The obtained two DNA fragments were ligated to the vector pDZ (Korean Patent No. 10-0924065 and International Publication No. 2008-033001), which had been digested with a restriction enzyme SalI, by using an infusion enzyme, and thereby a single vector for gene substitution, which includes a hisE promoter, was prepared, and the vector was named as "pDZ-hisE-pro-2mt". Additionally, the polynucleotide (500 bp) amplified using the primers of SEQ ID NOS: 6 and 11 and the polynucleotide (500 bp) amplified using the primers of SEQ ID NOS: 10 and 9 were obtained. The obtained two DNA fragments were ligated to the vector pDZ (Korean Patent No. 10-0924065 and International Publication No. 2008-033001), which had been digested with a restriction enzyme SalI, by using an infusion enzyme, and thereby a single vector for gene substitution, which includes a hisE promoter, was prepared, and the vector was named as "pDZ-hisE-pro-3mt". The information on the primer sequences used for the vector preparation is shown in Table 3 below.

TABLE 3

| SEQ ID NO | Primer | Sequence (5' to 3') |
|---|---|---|
| 4 | hisE-pro-2mt-AF | GATCCTCTAGAGTCGACTTCGACGAATCCCTCG |
| 5 | hisE-pro-2mt-AR | CGGTACATTATACCACACAACAGTTATCAATG |
| 6 | hisE-pro-2mt-BF | GTGGTATAATGTACCGAGTGAAGACATTTGAC |
| 7 | hisE-pro-2mt-BR | ATGCCTGCAGGTCGACTGATACCCAAATCGAG |
| 10 | hisE-pro-3mt-AR | CGGT<u>CCATTATA</u>CCACACAACAGTTATCAATG |
| 11 | hisE-pro-3mt-BF | GTGG<u>TATAATGG</u>ACCGAGTGAAGACATTTGAC |

EXAMPLE 4-2

Preparation of KFCC11074 into which Mutation is Introduced and Confirmation of Production Amounts of Glutamic Acid and Glycine The vectors for gene substitution (i.e., pDZ-hisE-pro-2mt and pDZ-hisE-pro-3mt), which had been prepared in Example 4-1, were introduced into the strain KFCC11074 by electroporation to prepare "KFCC11074_Pro(2mt)_hisEG" and "KFCC11074_Pro(3mt)_hisEG", which are the glutamic acid- and glycine-producing strains into which the mutation was introduced.

Specifically, it was prepared through transformation (Appl. Microbiol. Biotechnol., 1999, 52: 541-545), and the strain in which the vector was inserted on the chromosome by recombination of homologous sequences was selected on an agar nutrient medium containing kanamycin (25 mg/L). The selected primary strain was again subjected to a secondary crossover, and the strains into which the two or three target mutations were introduced were selected, respectively. The mutation (substitution) of the finally transformed strain was confirmed by sequencing after carrying out PCR using a pair of primers of SEQ ID NOS: 6 and 9.

Thereafter, the selected strains KFCC11074_Pro(2mt)_hisEG and KFCC11074_Pro(3mt)_hisEG were plated on a nutrient medium and cultured at 30° C. for 16 hours. A fermentation medium (25 mL), which had been pressurized and sterilized at 121° C. for 15 minutes, was dispensed into an Erlenmeyer flask (250 mL) for shaking, and then the strain cultured in the nutrient medium was inoculated and cultured for 48 hours. The culture conditions were set to 200 rpm, 37° C., and pH 8.0. The compositions of the nutrient medium and fermentation medium are as follows.

Nutrient Medium:
Glucose 1%, meat juice 0.5%, polypeptone 1%, sodium chloride 0.25%, yeast extract 0.5%, agar 2%, urea 0.2%, pH 7.2

Fermentation Medium:
Raw sugar 6%, calcium carbonate 5%, ammonium sulfate 2.25%, potassium monophosphate 0.1%, magnesium sulfate 0.04%, iron sulfate (10 mg/L), biotin (0.3 mg/L), thiamine hydrochloride (0.2 mg/L)

After completion of the culture, the production amounts of L-glutamic acid and glycine were measured using HPLC, and the measurement results are shown in Table 4 below.

TABLE 4

| Strain | L-Glutamic acid (g/L) | L-Glycine (mg/L) |
|---|---|---|
| KFCC11074 | 11.8 | 170 |
| KFCC11074_Pro(2mt)_hisEG | 11.7 | 203 |
| KFCC11074_Pro(3mt)_hisEG | 12.0 | 212 |

As shown in Table 4, it was confirmed that the concentration of L-glutamic acid produced by the Corynebacterium glutamicum strains KFCC11074_Pro(2mt)_hisEG and KFCC11074_Pro(3mt)_hisEG, into which the mutation was introduced, was similar to that produced by the Corynebacterium glutamicum strain KFCC11074 without the mutation.

On the other hand, it was confirmed that the concentration of glycine produced by the strains KFCC11074_Pro(2mt)_hisEG and KFCC11074_Pro(3mt)_hisEG was increased by 33 mg/L and 42 mg/L relative to that produced by the strain KFCC11074, respectively.

That is, it was confirmed that the mutation remarkably increased the glycine productivity while maintaining the L-glutamic acid productivity in the microorganisms with no significant effect thereon.

EXAMPLE 5

Preparation of Strains into which hisG Feedback Inhibition Release Mutation is Introduced and Confirmation of Productivity of Glutamic Acid and Glycine

EXAMPLE 5-1

Preparation of VectorInto which hisG Feedback Inhibition Release Mutation is Introduced Since it was confirmed through Examples 1-1 to 4-2 above that the glycine productivity of the strains was increased by the mutation in the promoter of the gene hisEG, the histidine feedback inhibition release mutation was introduced into the strains in order to maximize the effect of increasing the glycine productivity. Thereafter, the glycine productivity was confirmed.

Meanwhile, the genes hisE and hisG are composed of operons, and these genes are involved in the histidine biosynthesis pathway. In particular, since the HisG is feedback-inhibited by the product histidine, attempts were made to confirm whether the glycine productivity of the strains would be increased when the feedback inhibition release mutation is introduced to increase the activity of HisG.

Specifically, attempts were made to introduce the G233H and T235Q mutants known in the literature (Schendzielorz et al., 2014) into the gene hisG. A vector for gene substitution was constructed in order to substitute the $233^{rd}$ and $235^{th}$ amino acids of the hisG amino acid sequence of SEQ ID NO: 16 with H and Q, respectively. The gene fragments for constructing the vector were obtained by PCR using ATCC13869 genomic DNA as a template. Based on information on genes and adjacent nucleotide sequences of the Corynebacterium glutamicum (ATCC13869) registered in the National Institutes of Health GenBank (NIH GenBank), primers including the polynucleotides of SEQ ID NOS: 12, 13, 14, and 15 were prepared.

After denaturation at 95° C. for 5 minutes, PCR was carried out for a total of 30 cycles under the following conditions: denaturation at 95° C. for 30 seconds, annealing at 55° C. for 30 seconds, and polymerization at 72° C. for 1 minute. Thereafter, the polymerization reaction was carried out at 72° C. for 5 minutes. The polynucleotide (722 bp) amplified using the primers of SEQ ID NOS: 12 and 13 and the polynucleotide (798 bp) amplified using the primers of SEQ ID NOS: 14 and 15 were obtained. The two obtained DNA fragments were ligated to the vector pDZ (Korean Patent No. 10-0924065 and International Publication No. 2008-033001), which had been digested with a restriction enzyme SalI, by using an infusion enzyme, and thereby a single vector (1.5 kbp) for gene substitution, which includes the polynucleotide containing the hisG(G233H/T235Q) mutant, was prepared, and the vector was named as "pDZ-hisG(G233H/T235Q)". The information on the primer sequences used for the vector preparation is shown in Table 5 below.

trations of L-glutamic acid and glycine in each medium were measured. The measured concentrations of L-glutamic acid and glycine are shown in Table 6 below.

TABLE 6

| Strain | L-Glutamic acid (g/L) | L-Glycine (mg/L) |
|---|---|---|
| KFCC11074_hisG(G233H/T235Q) | 10.3 | 445.7 |
| KFCC11074_hisG(G233H/T235Q)_Pro(2mt)_hisEG | 10.1 | 760.0 |
| KFCC11074_hisG(G233H/T235Q)_Pro(3mt)_hisEG | 10.3 | 783.2 |

As shown in Table 6, it was confirmed that the concentration of L-glutamic acid produced by the *Corynebacterium glutamicum* strains KFCC11074_hisG(G233H/T235Q)_Pro(2mt)_hisEG and KFCC11074_hisG(G233H/T235Q)_Pro(3mt)_hisEG, into which the hisEG promoter mutation was introduced, was similar to that produced by the *Corynebacterium glutamicum* strain KFCC11074_hisG(G233H/

TABLE 5

| SEQ ID NO | Primer | Sequence (5' to 3') |
|---|---|---|
| 12 | hisG(G233H/T235Q)-AF | GATCCTCTAGAGTCGACCCCAAACAAGGGCTCGC |
| 13 | hisG(G233H/T235Q)-AR | CGTGCCAGTGGGGATACCTGTGGGTGGG |
| 14 | hisG(G233H/T235Q)-BF | AACCCCAGGCCTATCCCACCCACAGGTATC |
| 15 | hisG(G233H/T235Q)-BR | ATGCCTGCAGGTCGACGCAAGGTTGGCAACAAC |

EXAMPLE 5-2

Preparation and Evaluation of hisE Promoter-Mutated Strain into which Mutation for HisG Feedback Inhibition Release is Introduced "pDZ-hisG(G233H/T235Q)", the vector for gene substitution which had been prepared through Example 5-1 above, was introduced into the strain KFCC11074 to prepare the strain KFCC11074_hisG(G233H/T235Q) having HisG feedback inhibition release. In addition, the vector was introduced into the strains KFCC11074_Pro(2mt)_hisEG and KFCC11074_Pro(3mt)_hisEG to prepare the strains KFCC11074_hisG(G233H/T235Q)_Pro(2mt)_hisEG and KFCC11074_hisG(G233H/T235Q)_Pro(3mt)_hisEG, into which the mutation of the present disclosure was introduced.

Specifically, the strains were prepared through transformation (Appl. Microbiol. Biotechnol., 1999, 52: 541-545), and the strains in which the vector was inserted on the chromosome by recombination of homologous sequences were selected on an agar nutrient medium containing kanamycin (25 mg/L). The selected primary strains were again subjected to a secondary crossover, and the strains into which the target G233H/T235Q mutations are introduced were selected. The mutation (substitution) of the finally transformed strains was confirmed by sequencing after carrying PCT using a pair of primers of SEQ ID NOS: 12 and 15.

Thereafter, the selected strains KFCC11074_hisG(G233H/T235Q) and KFCC11074_hisG(G233H/T235Q)_Pro(2mt)_hisEG were cultured in the same manner as in Example 4-2. After completion of the culture, the concentrations T235Q) into which only the HisG feedback inhibition release mutation was introduced.

Meanwhile, it was confirmed that the concentration of glycine produced by the strains KFCC11074_hisG(G233H/T235Q)_Pro(2mt)_hisEG and KFCC11074_hisG(G233H/T235Q)_Pro(3mt)_hisEG were remarkably increased by 314.3 mg/L relative to that produced by the strain KFCC11074_hisG(G233H/T235Q).

That is, it was confirmed that the mutations remarkably increased the glycine productivity while maintaining the L-glutamic acid productivity in the microorganisms with no significant effect thereon. In addition, such results were exhibited by the increased activities of hisE and hisG.

EXAMPLE 6

Preparation of Fermented Composition for Preparation of Seasoning Products

As described above, it was confirmed that the strains containing the nucleotide of the present disclosure showed an increased ability to produce glycine without having no significant effect on the L-glutamic acid. Therefore, an attempt was made to prepare a fermented composition using a microorganism of the genus *Corynebacterium* containing the nucleotides of the present application.

For example, it was attempted to prepare the fermented composition using glutamic acid, which is basically a well-known seasoning material, as an active ingredient, and the fermentation strain and fermentation processes were controlled to increase the proportions of other by-product ingredients of the seasoning materials for the purpose of increasing the constitution of the rich taste.

EXAMPLE 6-1

Preparation of Fermented Composition Using 5 L Fermenter

Specifically, fermented compositions were prepared using a 5 L fermenter for the strains used in Example 5.

All of the ingredients used in the preparation of the culture media used were those corresponding to the food grade.

Primary seed medium was prepared as follows:

Glucose (1%), Peptone (10 g), Yeast Extract (1%), Peptone (1%), Ammonium Sulfate (0.1%), NaCl (0.25%), $KH_2PO_4$ (0.15%), $K_2HPO_4$ (0.15%), pH (8.0)

Secondary seed medium was prepared as follows:

Organic Raw Sugar (4.6% with a purity of 98.5%), Magnesium Sulfate (0.05%), Yeast Extract (0.5%), $KH_2PO_4$ (0.2%), Iron Sulfate (0.002%), Biotin (1 mg/L), Thiamine HCl (2 mg/L), a small amount of an anti-foaming agent, pH (7.2)

Fermentation medium was prepared as follows:

Organic Raw Sugar (4% with a purity of 98.5%), Magnesium Sulfate (0.03%), Yeast Extract (1%), Phosphoric Acid (0.22%), KOH (0.4%), Biotin (0.2 mg/L), Thiamine HCl (0.6 mg/L), Manganese Sulfate (0.002%), Iron Sulfate (0.002%), Zinc Sulfate (0.002%), Copper Sulfate (0.006%), a small amount of an anti-foaming agent, pH (7.4)

The primary seed medium (50 mL) was dispensed into each 500 mL shaking Erlenmeyer flask, autoclaved at 121° C. under pressure for 20 minutes. Then, each seed culture was inoculated and incubated with shaking at a rotation speed of 200 rpm, at 30° C. for 5 to 7 hours.

The secondary seed medium was prepared in an amount of 0.25 L in a 1.5 L test fermenter, autoclaved at 121° C. under pressure for 20 minutes, and cooled. Then, the primary seed medium (50 mL) was inoculated and incubated at a rotation speed of 900 rpm, at 31.5° C. for 15 hours.

The fermentation medium was prepared in an amount of 0.25 L in a 5 L test fermenter, autoclaved at 121° C. under pressure for 20 minutes, and cooled. Then, the secondary seed medium (0.26 L) was inoculated thereto and incubated at a rotation speed of 900 rpm, at 30° C. to 34° C.

While culturing under the above conditions, the pH of the fermentation culture was continuously adjusted using 28% ammonia water to be in the range of 7.0 to 7.4 during the culture of the *Corynebacterium glutamicum*. When the concentration of the residual sugar in the culture became in the range of 0.5% to 1.5%, sterilized organic raw sugar was continuously added to continue the culture until the total amount of the sugar added became 30% to 34% of the amount of the fermented broth.

As a result, as shown in Table 7 above, it was confirmed that although there was no significant difference in the amount of glutamic acid production between the two strains, the amount of glycine in the fermented broth produced by the *Corynebacterium glutamicum* KFCC11074_hisG(G233H/T235Q)_Pro(3mt)_hisEG strain, in which the mutation was introduced, was significantly increased.

Even in a case where a fermented composition was prepared using a 3 kL fermenter, there was no significant difference in the amount of glutamic acid production between the two strains. However, the *Corynebacterium glutamicum* KFCC11074_hisG(G233H/T235Q)_Pro(3mt)_hisEG strain, in which the mutation was introduced, showed a significant increase in the amount of glycine compared to the KFCC11074 strain (i.e., 0.2 g/L vs 3.2 g/L) although there was no significant difference in the amount of glutamic acid production between the two strains (64.2 g/L vs 73 g/L).

From the foregoing, one of ordinary skill in the art to which the present disclosure pertains will be able to understand that the present disclosure may be embodied in other specific forms without modifying the technical concepts or essential characteristics of the present disclosure. In this regard, the exemplary embodiments disclosed herein are only for illustrative purposes and should not be construed as limiting the scope of the present disclosure. On the contrary, the present disclosure is intended to cover not only the exemplary embodiments but also various alternatives, modifications, equivalents, and other embodiments that may be included within the spirit and scope of the present disclosure as defined by the appended claims.

[Accession Number]

Depository Institution: Korean Culture Center of Microorganisms

Accession Number: KCCM12226P

Date of Deposit: Feb. 28, 2018

Depository Institution: Korean Culture Center of Microorganisms

Accession Number: KCCM12457P

Date of Deposit: Mar. 14, 2019

TABLE 7

| Strain | Results of Analysis (g/L) | | | | | | |
|---|---|---|---|---|---|---|---|
| | Active Ingredient | | | By-product | | | |
| | Solid | Glutamic Acid | Glycine | Amino Aic | Organic Acid | Residual Sugar | Ions |
| KFCC11074 | 140.2 | 64.2 | 0.18 | 11.5 | 3.5 | 12.0 | 11.1 |
| KFCC11074_hisG(G233H/T235Q)_Pro(3mt)_hisEG | 147.3 | 59.0 | 2.43 | 16.4 | 2.7 | 15.1 | 10.7 |

The invention claimed is:

1. A polynucleotide having promoter activity, comprising a nucleotide sequence having at least 70% identity to SEQ ID NO: 1, wherein
the nucleotides corresponding to the 53$^{rd}$ and 55$^{th}$ nucleotides of SEQ ID NO: 1 are substituted with T; or
the nucleotides corresponding to the 53$^{rd}$ and 55$^{th}$ nucleotides of SEQ ID NO: 1 are substituted with T and the nucleotide corresponding to the 60$^{th}$ nucleotide of SEQ ID NO: 1 is substituted with G.

2. The polynucleotide according to claim 1, wherein the polynucleotide comprises of the nucleotide sequence of SEQ ID NO: 2 or 3.

3. The polynucleotide according to claim 1, comprising a nucleotide sequence having at least 80% identity to SEQ ID NO: 1.

4. The polynucleotide according to claim 1, comprising a nucleotide sequence having at least 83% identity to SEQ ID NO: 1.

5. The polynucleotide according to claim 1, comprising a nucleotide sequence having at least 84% identity to SEQ ID NO: 1.

6. The polynucleotide according to claim 1, comprising a nucleotide sequence having at least 90% identity to SEQ ID NO: 1.

7. The polynucleotide according to claim 1, comprising a nucleotide sequence having at least 93% identity to SEQ ID NO: 1.

8. The polynucleotide according to claim 1, wherein the polynucleotide is operably linked to a gene encoding a target protein.

9. A vector comprising the polynucleotide of claim 1; and a gene encoding a target protein operably linked to the polynucleotide.

10. The vector according to claim 9, wherein the target protein is phosphoribosyl-ATP pyrophosphatase (HisE), ATP phosphoribosyltransferase (HisG), or a combination thereof.

11. A microorganism of the genus *Corynebacterium*, comprising the polynucleotide of claim 1; and a gene encoding a target protein operably linked to the polynucleotide.

12. The microorganism according to claim 11, wherein the polynucleotide comprises of the nucleotide sequence of SEQ ID NO: 2 or 3.

13. The microorganism according to claim 12, wherein the target protein is phosphoribosyl-ATP pyrophosphatase: (HisE), ATP phosphoribosyltransferase (HisG), or a combination thereof.

14. The microorganism according to claim 13, wherein, in the ATP phosphoribosyltransferase (HisG), the 233$^{rd}$ and 235$^{th}$ amino acids of the HisG amino acid sequence of SEQ ID NO: 16 are substituted with histidine (H) and glutamine (Q), respectively.

15. The microorganism according to claim 11, wherein the microorganism of the genus *Corynebacterium* is *Corynebacterium glutamicum*.

16. A method for producing a target substance, comprising:
culturing the microorganism of the genus *Corynebacterium* of claim 11 in a medium; and
recovering the target substance from the medium.

17. The method according to claim 16, wherein the target substance is an amino acid.

18. A method for preparing a fermented composition, comprising fermenting by culturing the microorganism of the genus *Corynebacterium* of claim 11 in a medium.

19. A culture medium comprising the microorganism of claim 11.

* * * * *